United States Patent
Xue et al.

(10) Patent No.: US 11,642,436 B2
(45) Date of Patent: May 9, 2023

(54) BIODEGRADABLE BONE GLUE

(71) Applicant: EVONIK OPERATIONS GMBH, Essen (DE)

(72) Inventors: Teng Xue, Tianjin (CN); Gianluigi Luppi, Düsseldorf (DE); Natalia Ruggeri Savietto, Frankfurt am Main (DE); Howard K. Bowman, III, Birmingham, AL (US); Paul Joseph Spencer, Oberursel (DE); Andreas Karau, Gelnhausen (DE); Jian-Feng Zhang, Vestavia, AL (US); Rosario Lizio, Dieburg (DE); Marshall Scott Jones, Bessemer, AL (US)

(73) Assignee: Evonik Operations GmbH, Essen (DE)

( * ) Notice: Subject to any disclaimer, the term of this patent is extended or adjusted under 35 U.S.C. 154(b) by 625 days.

(21) Appl. No.: 16/608,830

(22) PCT Filed: Apr. 27, 2018

(86) PCT No.: PCT/EP2018/060965
§ 371 (c)(1),
(2) Date: Oct. 26, 2019

(87) PCT Pub. No.: WO2018/197706
PCT Pub. Date: Nov. 1, 2018

(65) Prior Publication Data
US 2020/0197562 A1    Jun. 25, 2020

Related U.S. Application Data

(60) Provisional application No. 62/491,665, filed on Apr. 28, 2017.

(51) Int. Cl.
*A61L 24/00* (2006.01)
*B33Y 70/00* (2020.01)
(Continued)

(52) U.S. Cl.
CPC ............ *A61L 24/0042* (2013.01); *A61B 17/00491* (2013.01); *A61F 2/0095* (2013.01);
(Continued)

(58) Field of Classification Search
CPC combination set(s) only.
See application file for complete search history.

(56) References Cited

U.S. PATENT DOCUMENTS 6,420,454 B1 * 7/2002 Wenz ............... A61L 27/18
524/378
6,451,346 B1 9/2002 Shah et al.
(Continued)

FOREIGN PATENT DOCUMENTS

DE    19858891 A1    6/2000

OTHER PUBLICATIONS

PCT International Search Report and the Written Opinion of the International Searching Authority dated Jun. 20, 2018 corresponding to PCT Application No. PCT/EP2018/060965 filed Apr. 27, 2018 (11 pages).
(Continued)

*Primary Examiner* — Carlos A Azpuru
(74) *Attorney, Agent, or Firm* — Linda S. Li; Jason S. Ngui; Andrew H. Chung

(57) ABSTRACT

The present invention is directed to bioresorbable polymers to be used as bone and tissue adhesives. The present invention is also directed to the synthesis of bioresorbable polymeric molecules bearing adhesive moieties and the use of such compounds in methods to glue and stabilize fractured bones and damaged tissues. The present invention is also directed to the use of such compounds as adhesive sealants for applications in wound care. The present invention is also directed to the use of such compounds as biodegradable ink for applications in tissue engineering and
(Continued)

3D printing. The present invention also relates to the use of such compounds as drug delivery platforms.

8 Claims, 8 Drawing Sheets

(51) Int. Cl.
| | |
|---|---|
| B29C 64/106 | (2017.01) |
| A61B 17/00 | (2006.01) |
| A61F 2/00 | (2006.01) |
| A61L 24/04 | (2006.01) |
| A61L 27/18 | (2006.01) |
| A61L 27/54 | (2006.01) |
| A61L 27/58 | (2006.01) |
| C08G 63/685 | (2006.01) |
| C08G 63/692 | (2006.01) |
| C08G 63/695 | (2006.01) |
| B33Y 10/00 | (2015.01) |
| B33Y 80/00 | (2015.01) |
| B29K 67/00 | (2006.01) |
| B29K 71/00 | (2006.01) |
| B29K 105/00 | (2006.01) |
| B29L 31/00 | (2006.01) |

(52) U.S. Cl.
CPC ......... *A61L 24/0015* (2013.01); *A61L 24/046* (2013.01); *A61L 27/18* (2013.01); *A61L 27/54* (2013.01); *A61L 27/58* (2013.01); *B29C 64/106* (2017.08); *B33Y 70/00* (2014.12); *C08G 63/6852* (2013.01); *C08G 63/6922* (2013.01); *C08G 63/6952* (2013.01); *A61B 2017/00495* (2013.01); *B29K 2067/043* (2013.01); *B29K 2067/046* (2013.01); *B29K 2071/02* (2013.01); *B29K 2105/0035* (2013.01); *B29K 2995/006* (2013.01); *B29L 2031/753* (2013.01); *B33Y 10/00* (2014.12); *B33Y 80/00* (2014.12)

(56) References Cited

U.S. PATENT DOCUMENTS

| | | | |
|---|---|---|---|
| 8,614,190 | B2 | 12/2013 | Peng et al. |
| 2012/0010139 | A1 | 1/2012 | Peng et al. |

OTHER PUBLICATIONS

Pan H. et al: "Polydopamine-assisted BMP-2-derived peptides immobilization on biomimetic copolymer", Colloids and Surfaces B:Biomaterials, vol. 142, 2016, pp. 1-9.

Swami A. et al: "Engineered nanomedicine for myeloma and bone microenvironment targeting", Proccedings of the National Academy of the United States of America, vol. 111, Jul. 15, 2014 (Jul. 15, 2014), pp. 10287-10292.

Jeong B. et al: "Biodegradable thermosensitive micelles of PEG-PLGA-PEG triblock copolymers", Colloids and Surfaces B:Biointerfaces, vol. 16, 1999, pp. 185-193.

\* cited by examiner

BIODEGRADABLE BONE GLUE

This Application is a 35 U.S.C. § 371 U.S. national stage of PCT International Application No. PCT/EP2018/060965, filed Apr. 27, 2018, which claims the benefit of U.S. Provisional Patent Application No. 62/491,665, filed Apr. 28, 2017, the contents of each of which are hereby incorporated by reference in their entirety into this application.

FIELD OF THE INVENTION

This invention relates to bioresorbable polymers for use as bone and tissue adhesives. The invention further relates to the synthesis of bioresorbable polymeric molecules bearing adhesive moieties and the use of such compounds to glue and stabilize fractured bones and damaged tissues. The invention also relates to the use of such compounds as adhesive sealants for applications in wound care. The invention relates also to the use of such compounds as biodegradable ink for applications in tissue engineering and 3D printing. The invention also relates to the use of such compounds as drug delivery platforms.

BACKGROUND OF THE INVENTION

Currently, the most common methodologies for fixation of fractured bones and damaged tissues rely mainly on the use of mechanical and rigid means. Depending on the area of application, fixation devices of choice can be nails, screws, plates, etc. Even though these methods can be advantageous for stabilizing and healing thick and robust bones such as long bones, the use of internal fixation devices may be detrimental when they are implemented to heal smaller regions and more complex bones in the upper and lower extremities (Hoffmann, B., Volkmer, E., Kokott, A. et al. J Mater Sci: Mater Med (2009) 20: 2001. doi:10.1007/s10856-009-3782-5; Fortschr Kiefer Gesichtschir. 1991; 36:30-3). In these cases, the application procedures can cause further fractures due to the forces applied to small area fragments which will lead to complication fragments (International Journal of Oral and Maxillofacial Surgery [2004, 33(4):377-381]; Compend Contin Educ Dent. 2005; 8:565-571; J Oral Maxillofac Surg. 1991; 49:683-688; J Craniofac Surg. 1990; 1:35-52; J Oral Maxillofac Surg. 1999; 57:130-134). Therefore, the use of bioresorbable adhesives that have the capability to glue together small bone fragments and soft tissues with minimum invasive surgery is of great interest for the scientific and medical community. The development of such adhesive systems is extremely beneficial when it comes to supporting the fixation of medical devices in open surgeries. This system enables a more homogeneous weight distribution between bone fragments and an easier application procedures than the standard methods which normally involve the drilling of pilot holes with consequent risks of injures to anatomical structures such as vessels or nerves that leads to complications, extended hospitalization time, and elevated costs. Moreover, the use of such materials can be extended to a vast range of applications, including load-bearing bones, bone fillers, bone putties, dental, drug delivery, additive manufacturing, 3D printing etc.

To date, some examples have been reported in literature that allow satisfactory mechanical strength combined with the appropriate biocompatibility and biodegradability characteristics for use with soft tissues (Spotnitz W D: Fibrin sealant: past, present, and future: a brief review. World J Surg 2010, 34(4):632-634). Despite many efforts towards the development of similar systems for applications with bones, mainly non-biodegradable bone cements are currently commercialized. The use of bioresorbable glues in this field is of great interest due to the possibility of performing minimally invasive surgeries and addresses the need of efficiently joining small bones, e.g. extremities, ear bones, etc. The use of fully biodegradable glues does not only help stabilize small bones where the use of internal fixation devices is not practicable, but also avoids any additional surgery aimed at removing the implanted internal fixation devices.

The current landscape of adhesive systems utilized for in-vivo applications can be divided in two main categories: 1) synthetic glues and 2) biological derivative/inspired glues.

One of the most reported classes of synthetic adhesives for the stabilization of biological tissues is alkyl-cyanoacrylates. Although a wide class of cyanoacrylate adhesives have been successful commercialized in the field of wound care, the development of commercial cyanoacrylate glues for applications with internal biological tissues still represents a challenge because of the reported toxic side effects.

A wide class of polymethylmethacrylate (PMMA) materials has been developed for application as bone cements. Since PMMA bone cements have little to no intrinsic adhesion to bones, especially in wet conditions, their fixation properties are instead caused by the formation of a mechanical interlock between the porous bones and the medical implant during the hardening of the material (D. F. Farrar/International Journal of Adhesion & Adhesives 33 (2012) 89-97).

Polyurethanes represent another important class of materials for medical applications. Polynovo Biomaterials has developed a liquid gel called NovoSorb, which is similar to glue and is easily injected into the body. Applied at the fracture, the gel cures into a biodegradable polyurethane based polymer that glues the fractured bone together and mechanically supports it while the polymer aids the healing process (Adhikari Raju et all. Biodegradable injectable polyurethanes: Synthesis and evaluation for orthopedic applications—Biomaterials (2008), 29(28), 3762-3770). Cohera Medical Inc. has developed TissuGlu, a synthetic lysine-based urethane adhesive that received FDA approval for surgical internal use. Cohera Medical Inc. has also recently received FDA approval to begin clinical trials of its Sylys surgical sealant for application in anastomotic leakage reduction. However, they have not emphasized it for its use in bone adhesive applications.

As an alternative to the use of synthetic adhesives, the scientific community has developed great interests in the development of viable biologically inspired adhesives. The main challenge in this regard is the low mechanical and adhesive strength that biologically inspired adhesives normally offer in wet environments (D. F. Farrar/International Journal of Adhesion & Adhesives 33 (2012) 89-97). However, in nature a few examples are found that show high mechanical and adhesion strength of natural adhesives even when applied in wet environments. Mussels and sea worms secrete natural mucus which is able to strongly adhere to highly wet surfaces. The high proportions of catechol and organophosphate moieties in such biomaterials have inspired the scientific community to synthetically reproduce such systems exploiting the adhesion properties of catecholes and organophosphates (The Journal of Experimental Biology 207, 4727-4734 Published by The Company of Biologists 2004 doi:10.1242/jeb.01330; Timothy J Deming, Current Opinion in Chemical Biology 1999, 3:100-105).

In this regard, naturally-derived adhesive poly (DHHCA-co-3HPPA) copolymer (DHHCA=3,4-dihydroxyhydrocinnamic acid, 3HPPA=3-(3-hydroxyphenyl) propionic acid has been developed and showed superb adhesion force due to the strong main chain composed by natural aromatic rings. The adhesive mechanism of this adhesive is originated from mussel adhesion in nature. (Patent WO2015068503).

Bioresorbable polymers based on PEG and DOPA as bone adhesive have been developed. The functionalized PEG can also be processed via in-situ oxidative crosslinking to form hydrogels with increased mechanical strength (Patent U.S. 2012/0156164). They use natural polymers as backbones such as gelatin, chitosan, heparin, cellulose, dextran, dextran sulfate, chondroitin sulfate, keratan sulfate, dermatan sulfate, alginate, collagen, albumin, fibronectin, laminin, elastin, vitronectin, hyaluronic acid, and fibrinogen etc. The use of natural polymers results in potentially lower mechanical properties, and can also trigger a biological response; and therefore, their in-vivo application need to be properly evaluated.

A multifunctional biomaterial based on polysaccharides (pullulan) functionalized with phosphate moieties with the capacity bond to hard tissues such as bones and teeth has been developed (Biomedical Materials, 2015, 10(6), 1-9). They also use natural polymers such as pullulan as backbones. However, the use of natural polymers results in potentially lower mechanical properties. Natural polymers can also trigger a biological response. Therefore, their in-vivo application need to be properly evaluated.

Even though many different approaches have been pursued to achieve the desired mechanical and biocompatibility properties, a viable bioresorbable adhesive system that meets all medical needs is still missing.

SUMMARY OF THE INVENTION

It is an object of the present invention to provide bioresorbable polymers that can be used as bone and tissue adhesives, adhesive sealants for wound care, fillers in biological tissues, drug delivery platforms and biodegradable ink for applications in tissue engineering and 3D printing.

The present invention is directed to a novel compound of Formula I wherein:
R is:

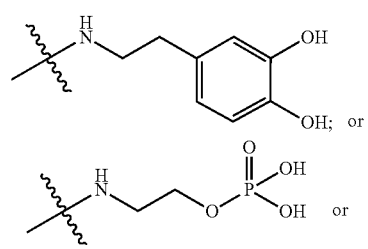

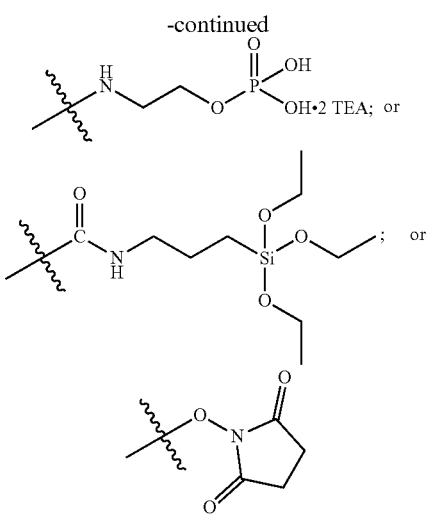

wherein:
m is between 4 and 90;
n is between 5 and 200;
x is between 1 and 200; and
y is between 0 and 200.

In one aspect, disclosed is a composition comprising: a bioresorbable polymer of Formula I, or a mixture thereof; a solvent; and a non-solvent.

In another aspect, disclosed is a composition comprising: a bioresorbable polymer of Formula I, or a mixture thereof; a solvent; a non-solvent; and an additive.

In still another aspect, disclosed is a composition comprising: a bioresorbable polymer of Formula I, or a mixture thereof; a solvent; a non-solvent; an additive; and wherein the additive is dissolved in the non-solvent.

In still another aspect, disclosed is a composition comprising: a bioresorbable polymer of Formula I, or a mixture thereof; a solvent; a non-solvent; and an antimicrobial agent, antibacterial agent, or a mixture thereof.

In still another aspect, disclosed is a composition comprising: a bioresorbable polymer of Formula I, or a mixture thereof; a solvent; a non-solvent; an additive; an antimicro-

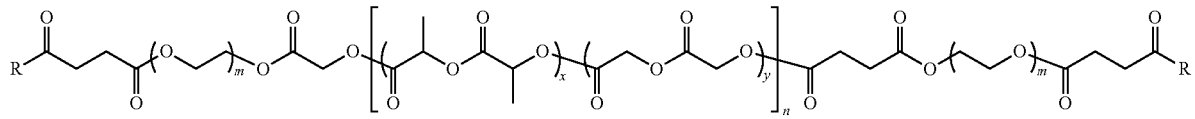

(Formula I)

bial agent, antibacterial agent, or a mixture thereof; and wherein the additive is dissolved in the non-solvent.

In still another aspect, disclosed process for preparing a bioresorbable polymer of Formula I comprising the steps of mixing a polymer backbone with a functional group precursor to form a mixture; and adding a linker to the mixture to form the bioresorbable polymer.

In still another aspect, disclosed is a dental membrane comprising a polymer backbone, a bioresorbable polymer of Formula I, or a mixture thereof; a solvent; and a non-solvent.

In still another aspect, disclosed is a 3D printed part comprising a polymer backbone, a bioresorbable polymer of Formula I, or a mixture thereof; a solvent; a non-solvent; and additive.

In still another aspect, disclosed is a process for producing a 3D printed part containing a polymer backbone, a bioresorbable polymer of Formula I, or a mixture thereof; the process comprising: (a) providing polymer backbone bioresorbable polymer of Formula I, or a mixture thereof; (b) adding polymer backbone, bioresorbable polymer of Formula I, or a mixture thereof to a solvent to form a polymer solution; (c) adding or contacting an additive to the polymer solution; (d) printing the polymer solution through a print head to form multiple layers of the 3D printed part; and (e) setting the 3D printed part.

In still another aspect, disclosed is a bioprinted part comprising a polymer backbone, a bioresorbable polymer of Formula I, or a mixture thereof; a solvent; a non-solvent; an additive; and a bioactive agent.

In still another aspect, disclosed is a process for producing a bioprinted part containing a polymer backbone, a bioresorbable polymer of Formula I, or a mixture thereof; the process comprising: (a) providing polymer backbone, bioresorbable polymer of Formula I, or a mixture thereof; (b) adding polymer backbone, bioresorbable polymer of Formula I, or a mixture thereof to a solvent to form a polymer solution; (c) adding or contacting an additive to the polymer solution; (d) printing the polymer solution through a print head to form multiple layers of the bioprinted part; (e) setting the bioprinted printed part; and wherein either step (b) or (c) further comprises adding a bioactive agent.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
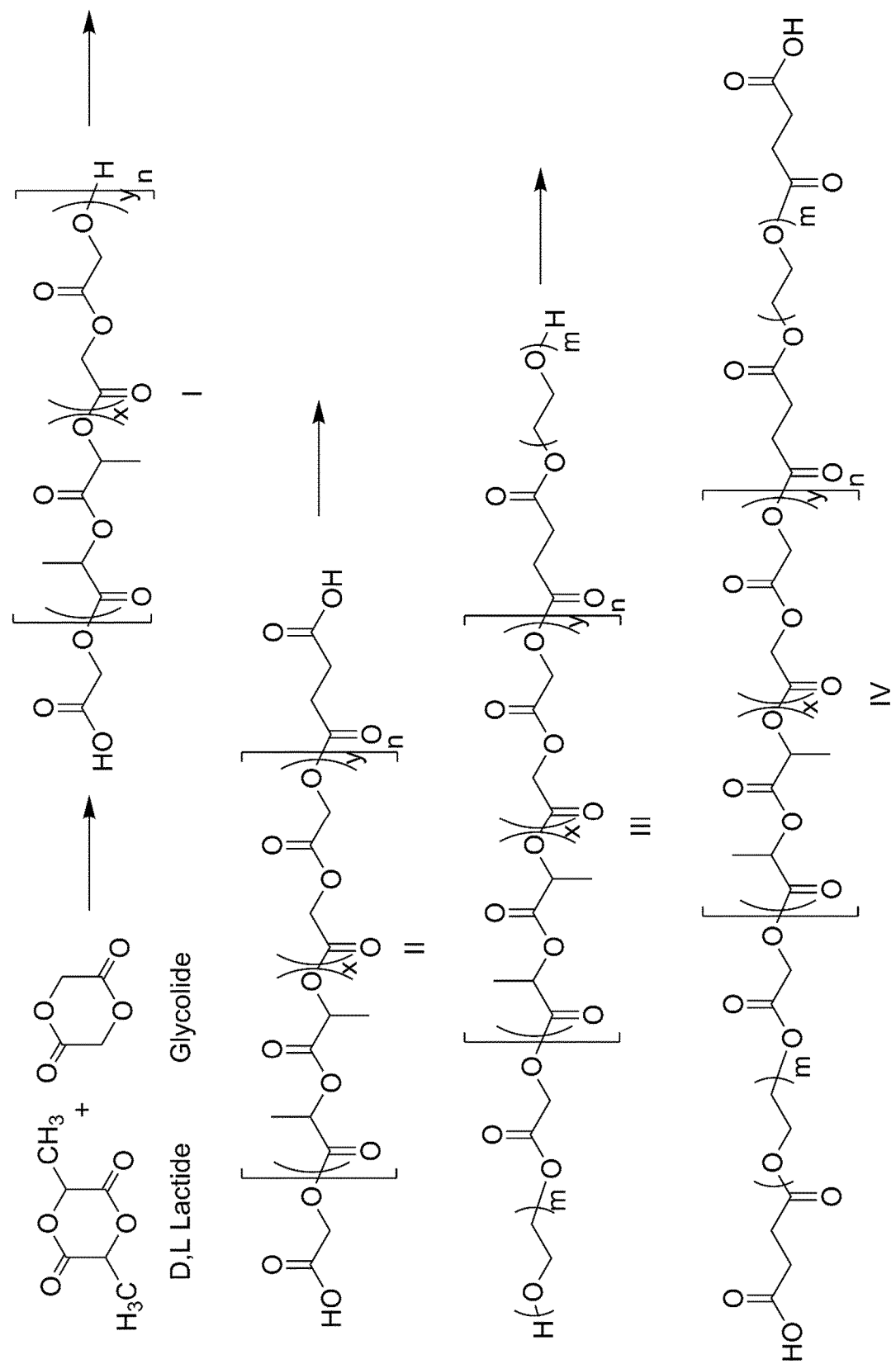
FIG. 1 is a reaction scheme showing the synthesis of the polymer backbone.

Before the present compounds and processes are disclosed and described, it is to be understood that the aspects described herein are not limited to specific processes, compounds, synthetic methods, articles, devices, or uses as such can, of course, vary. It is also to be understood that the terminology used herein is for the purpose of describing particular aspects only and, unless specifically defined herein, is not intended to be limiting.

Disclosed herein are bioresorbable polymers that shows adhesive properties to human bones, soft tissues, and metals. The polymers synthetized is composed of a triblock copolymer A-B-A backbone, where A is polyethylene glycol with a range of Mn from 200 Da to 4000 Da. B is poly-D,L, lactide-glycolide-copolymer with a range of Mn from 1000 Da to 15000 Da. In the backbone, there are chain terminals designated as R groups. The synthesized polymers bear active functional moieties at the R groups with the function of covalently binding human bones, soft tissues, and metals.

The disclosed bioresorbable polymers provide the advantage of a biodegradable profile, which will provide for easier application procedures than the standard methods, which normally involve the drilling of pilot holes with consequent risks of injuries to anatomical structures such as vessels or nerves that leads to complications, extended hospitalization time, and elevated costs. Another advantage of bioresorbable polymers is that it can be extended to a vast range of applications, including load-bearing bones, bone fillers, bone putties, dental, drug delivery, additive manufacturing, 3D printing etc.

Definition of Terms

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "wt. %" means weight percent.

The term "w/w" means weight per weight.

For the purposes of the present invention, the term "biodegradable" refers to polymers that dissolve or degrade in vivo within a period of time that is acceptable in a particular therapeutic situation. Such dissolved or degraded product may include a smaller chemical species. Degradation can result, for example, by enzymatic, chemical and/or physical processes. Biodegradation takes typically less than five years and usually less than one year after exposure to a physiological pH and temperature, such as a pH ranging from 6 to 9 and a temperature ranging from 22° C. to 40° C.

For the purposes of the present invention, the term "3D printed part" refers to a part printed by a 3D printer. A 3D printer includes, but are not limited to, bioplotter, fused filament fabrication (FFF), selective laser sintering (SLS), and stereolithography (SLA). A 3D printed part can also be a bioprinted part.

The term "biological tissues" include, but are not limited to, human soft tissues, skin, subcutaneous layer, mucous membranes, cartilage, ligaments, tendons, muscle tissues, blood vessels, human organs, cardiac muscle tissues, heart valves, nervous tissues, pericardium, pleurae, and peritoneum.

The term "dental membrane application" include, but are not limited to applications of dental implants, guided periodontal regeneration, and periodontal pocket applications.

Suitable biodegradable polymers for the backbone of the invention include without limitation poly(lactide), a poly (glycolide), a poly(lactide-co-glycolide), a poly(caprolactone), a poly(orthoester), a poly(phosphazene), a poly(hydroxybutyrate) a copolymer containing a poly (hydroxybutarate), a poly(lactide-co-caprolactone), a polycarbonate, a polyesteramide, a polyanhydride, a poly (dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations thereof.

The biodegradable polymer can comprise one or more residues of lactic acid, glycolic acid, lactide, glycolide, caprolactone, hydroxybutyrate, hydroxyvalerates, dioxanones, polyethylene glycol (PEG), polyethylene oxide, or a combination thereof. In some aspects, the biodegradable polymer comprises one or more lactide residues. The polymer can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly (DL-lactide); and poly(lactide-co-glycolide), including poly (L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

When poly(lactide-co-glycolide), poly(lactide), or poly (glycolide) is used, the amount of lactide and glycolide in the polymer can vary. For example, the biodegradable polymer can contain 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide).

In the preparation of the molecular backbone, the polymerization steps can be carried out using a catalytically-effective amount of a catalyst. The formation of the polymer of cyclic esters can be carried out with any suitable catalyst known to polymerize cyclic esters. The polymerization catalyst can be metallic or non-metallic, including a variety of non-metallic organic catalysts. Suitable metal catalysts include zinc powder, tin powder, aluminum, magnesium and germanium, metal oxides such as tin oxide (II), antimony oxide (III), zinc oxide, aluminum oxide, magnesium oxide, titanium oxide (IV) and germanium oxide (IV), metal halides such as tin chloride (II), tin chloride (IV), tin bromide (II), tin bromide (IV), antimony fluoride (III), antimony fluoride (V), zinc oxide, magnesium chloride and aluminum chloride, sulfates such as tin sulfate (II), zinc sulfate and aluminum sulfate, carbonates such as magnesium carbonate and zinc carbonate, borates such as zinc borates, organic carboxylates such as tin acetate (II), tin octanoate (II), tin lactate (II), zinc acetate and aluminum acetate, organic sulfonates such as tin trifluoromethane sulfonate (II), zinc trifluoromethane sulfonate, magnesium trifluoromethane sulfonate, tin (II) methane sulfonate and tin (II) p-toluene sulfonate. Dibutyltin dilaurate (DBTL), Sb2O3, Ti(IV)bu, Ti(IV)iso, and others. The polymerization catalyst can also be a non-metallic acids, such as an organic acid. The organic acid can be a weak acid or a strong acid. Examples of suitable organic acids include acetic acid, methane sulfonic acid, ethane sulfonic acid, 1-propane sulfonic acid, 1-butane sulfonic acid, trifluoromethane sulfonic acid, benzene sulfonic acid, p-toluene sulfonic acid, p-xylene-2-sulfonic acid, naphthalene-1-sulfonic acid and naphthalene 2-sulfonic acid, and stronger acids such as hydrochloric acid, sulfuric acid, glacial acetic acid, and phosphoric acid. In a preferred aspect of the process, the polymerization catalyst is tin octanoate (II). In the preparation of the molecular backbone, the polymerization steps can be carried out also using a chain initiator. Various initiator agents that can be used for the coupling reaction include, but are not limited to, glycolic acid, polyethylene glycol (PEG), and polyols.

The addition of the catalyst in the reaction mixture can be accomplished by adding the catalyst neat or dissolved in a solvent. Suitable solvents that can be used for dissolving the catalyst include, but not limited to, dimethyl sulphoxide, dimethyl formamide, and toluene.

The process comprises polymerizing a cyclic esters by heating a molten reaction mixture comprising the cyclic ester at a temperature of from about 100° C. to about 300° C. for a time ranging from about 0.5 hours to about 24 hours to form the polymeric ester in the molten reaction mixture.

According to this aspect of the process, the cyclic esters are heated at a temperature of from about 80° C. to about 250° C., preferably from about 100° C. to about 200° C., under reduced pressure, atmospheric pressure or sufficient pressure in the presence of an optional polymerization catalyst and initiator to conduct a polymerization reaction. After the formation of the polymers of the cyclic esters, the polymers can be undergone to a further carboxylation reaction step to form a carboxylated polymer. The carboxylation reaction can be carried out in the same or different reaction vessel. The two-step process can be carried out in a single reaction vessel (one-pot). The preparation of the carboxylate polymers can typically be accomplished by using organic cyclic anhydrides as reactant. Various organic cyclic anhydrides that can be used for the carboxylation of the polymeric backbone include, but are not limited to, succinic anhydride, glutaric anhydride, adipic anhydride, pimelic anhydride and maleic anhydride. Accordingly, the process comprises adding to the molten reaction mixture an appropriate amount of the cyclic anhydride and let the reaction mixture stir for a time ranging from about 0.5 hours to about 72 hours at a temperature of from about 80° C. to about 250° C., preferably from about 100° C. to about 200° C. to form the carboxylated polymer. The residual monomers and cyclic anhydride are distilled away from the reaction at a pressure of about 1 torr to 10 torr, preferably from 1 torr to 5 torr. The carboxylated polymer is removed from the reaction vessel and purified by precipitation. For example, the carboxylated polymer is dissolved in a solvent and then precipitated by adding a non-solvent for the carboxylated polymer. Various organic solvents that can be used as solvent for the carboxylated polymer include, but not limited to, acetone, chloroform, dichloromethane, dimethylsulphoxide, dimethyl formamide. Various solvents that can be used as a non-solvent for the carboxylated polymer include, but not limited to, ethanol, methanol, water, cyclohexane, hexane, and pentane.

The coupling of the molecular backbone with the PEG moiety can typically be accomplished by using an activating agent to mediate the coupling reaction. Various activating agents that can be used for the coupling reaction include, but are not limited to, 1-ethyl-3-(3-dimethylaminopropyl)carbodiimide (EDC), dicyclohexylcarbodiimide (DCC), N,N-diisopropyl-carbodiimide (DIP), benzotriazol-lyl-oxy-tris-(dimethyl amino) phosphonium hexa-fluorophosphate (BOP), N-dimethyl-amino pyridine (DMAP) hydroxybenzotriazole (HOBt), and N-methylmorpholine (NMM), including a mixture thereof. The coupling reaction can be carried out in N-methylpyrrolidone (NMP), DMF or in Dichloromethane (DCM). Accordingly, the process comprises stirring a liquid reaction medium comprising the carboxylated polymer at a temperature of from about 20° C. to about 50° C. for a time ranging from about 0.5 hours to about 72 hours to form the triblock-copolymer in the liquid reaction medium.

The triblock-copolymer is removed from the liquid reaction medium by precipitation, for example by adding a non-solvent for the triblock-copolymer to precipitate the triblock-copolymer out from the mixture or by recrystallizing the triblock-copolymer. The triblock-copolymer can also be recrystallized using a solvent such as ethyl acetate, dichloromethane, chloroform, diethyl ether or a mixture thereof. The triblock-copolymer can also be further purified by separating it from a mixture by centrifugal precipitation or decantation. The triblock-copolymer can also be washed with a non-solvent for the triblock-copolymer such as cyclohexane, methanol, ethanol or ether.

The preparation of the carboxylate forms of the triblock-copolymers can typically be accomplished by using organic cyclic anhydrides as reactant. Various organic cyclic anhydrides that can be used for the carboxylation of the polymeric backbone include, but are not limited to, succinic anhydride, glutaric anhydride, adipic anhydride, pimelic anhydride and maleic anhydride. Accordingly, the process comprises stirring a liquid reaction medium comprising the molecular backbone at a temperature of from about 20° C. to about 50° C. for a time ranging from about 0.5 hours to about 72 hours to form the carboxylated triblock-copolymer in the liquid reaction medium.

The carboxylated triblock-copolymer is removed from the liquid reaction medium by precipitation, for example by adding a non-solvent for the carboxylated triblock-copolymer to precipitate the carboxylated triblock-copolymer out from the mixture or by recrystallizing the carboxylated triblock-copolymer. The carboxylated triblock-copolymer can also be recrystallized using a solvent such as ethyl acetate, dichloromethane, chloroform, diethyl ether or a mixture thereof. The carboxylated triblock-copolymer can also be further purified by separating it from a mixture by centrifugal precipitation or decantation. The carboxylated triblock-copolymer can also be washed with a non-solvent for the carboxylated triblock-copolymer such as cyclohexane, methanol, ethanol or ether.

The preparation of the functionalized forms of the polymers can typically be accomplished by using the desired amino, hydroxy or thiol functional moieties as reactant. The coupling of the carboxylated triblock-copolymer with the amino functional moiety can typically be accomplished by using an activating agent to mediate the coupling reaction. Various activating agents that can be used for the coupling reaction include, but are not limited to, 1-ethyl-3-(3-dimethylaminopropyl)carbodiimide (EDC), dicyclohexylcarbodiimide (DCC), N,N-diisopropyl-carbodiimide (DIP), benzotriazol-lyl-oxy-tris-(dimethyl amino) phosphonium hexafluorophosphate (BOP), N-Hydroxysuccinimide (NHS), N-dimethyl-amino pyridine (DMAP) hydroxybenzotriazole (HOBt), and N-methylmorpholine (NMM), including a mixture thereof. The coupling reaction can be carried out in N-methylpyrrolidone (NMP), DMF or in Dichloromethane (DCM). Accordingly, the process comprises stirring a liquid reaction medium comprising the molecular backbone at a temperature of from about 20° C. to about 50° C. for a time ranging from about 0.5 hours to about 72 hours to form the functionalized triblock-copolymer in the liquid reaction medium.

The functionalized triblock-copolymer is removed from the liquid reaction medium by precipitation, for example by adding a non-solvent for the functionalized triblock-copolymer to precipitate the functionalized triblock-copolymer out from the mixture or by recrystallizing the functionalized triblock-copolymer. The functionalized triblock-copolymer can also be recrystallized using a solvent such as acetone, ethyl acetate, dichloromethane, chloroform, diethyl ether or a mixture thereof. The functionalized triblock-copolymer can also be further purified by separating it from a mixture by centrifugal precipitation or decantation. The functionalized triblock-copolymer can also be washed with a non-solvent for the functionalized triblock-copolymer such as cyclohexane, ethanol or ether. In some aspects, the entire process, including the formation of the activated carboxylic ester is carried in a single reaction vessel as a one-pot process. In other aspects, the activated carboxylic ester can be isolated and/or purified before coupling process is carried out. Various purification methods for the activated carboxylic ester can be used, such as precipitation, or washing with a non-solvent, such as ether to remove unreacted reagents.

The preparation of the functionalized forms of the polymers can also be accomplished by using the desired isocyanate functional moieties as reactant. The coupling of the triblock-copolymer with the isocyanate functional moiety can typically be carried out using a catalytically-effective amount of a catalyst. The formation of the urethane group to link the triblock-copolymer to the functional moiety can be carried out with any suitable catalyst known to promote isocyanate reactivity. The reaction catalyst can be metallic or non-metallic, including a variety of non-metallic organic catalysts. Suitable metal catalysts include, but not limited to, organo tin compounds such as tin acetate (II), tin octanoate (II), tin lactate (II), tin (II) methane sulfonate and tin (II) p-toluene sulfonate, dibutyltin dilaurate (DBTL). The reaction catalyst can also be a non-metallic compound, such as an organic base. The organic base can be a weak base or a strong base. Examples of suitable organic base include, but are not limited to triethyl amine (TEA), DABCO (1,4-diazabicyclo[2.2.2]octane), dimethylcyclohexylamine (DMCHA), dimethylethanolamine (DMEA), 1,8-diazabicyclo [5.4.0]undec-7-ene (DBU) and 4-dimethylaminopyridine (DMAP).

Accordingly, the process comprises stirring a liquid reaction medium comprising the triblock-copolymer at a temperature of from about 20° C. to about 100° C. for a time ranging from about 0.5 hours to about 72 hours to form the functionalized triblock-copolymer in the liquid reaction medium.

The functionalized triblock-copolymer is removed from the liquid reaction medium by precipitation, for example by adding a non-solvent for the functionalized triblock-copolymer to precipitate the functionalized triblock-copolymer out from the mixture or by recrystallizing the functionalized triblock-copolymer. The functionalized triblock-copolymer can also be recrystallized using a solvent such as acetone, ethyl acetate, dichloromethane, chloroform, diethyl ether or a mixture thereof. The functionalized triblock-copolymer can also be further purified by separating it from a mixture by centrifugal precipitation or decantation. The functionalized triblock-copolymer can also be washed with a non-solvent for the carboxylated triblock-copolymer such as cyclohexane, methanol, ethanol or ether.

The m value of the bioresorbable polymer is between 4 and 90. Preferably, the m value of the bioresorbable polymer is between 7 and 25.

The n value of the bioresorbable polymer is between 5 and 200. Preferably, the n value of the bioresorbable polymer is between 15 and 100.

The x value of the bioresorbable polymer is between 1 and 200. Preferably, the x value of the bioresorbable polymer is between 15 and 100.

The y value of the bioresorbable polymer is between 0 and 200. Preferably, the y value of the bioresorbable polymer is between 4 and 35.

Suitable bioactive agents of use in the present invention may be any agent capable of having an effect when administered to an animal or human. In a particular embodiment, they include, but are not limited to, an organic molecule, an inorganic molecule, antiinfectives, cytotoxics, antihypertensives, antifungal agents, antipsychotics, antibodies, proteins, peptides, antidiabetic agents, immune stimulants, immune suppressants, antibiotics, antivirals, anticonvulsants, antihistamines, cardiovascular agents, anticoagulants, hormones, antimalarials, analgesics, anesthetics, nucleic acids, steroids, aptamers, hormones, steroids, blood clotting factors, hemopoietic factors, cytokines, interleukins, cells, colony stimulating factors, growth factors and analogs, fragments thereof and the like.

Suitable antimicrobial agents include, but are not limited to Penicillins, Penicillin V, Penicillin G, Amoxicillin, Ampicillin, Cloxacillin, Methicillin, Amoxicillin+Clavulanate (Augmentin), Ticarcillin+Clavulanate, Nafcillin, 1st Generation Cephalosporins, Cephalexin (Keflex), Cefazolin, Cefadroxil, (LEXie DROpped ZOLa), 2nd Generation Cephalosporins, Ceflaclor, Cefuroxime, (LACking URine), 3rd Generation Cephalosporins, Cefotaxime, Cefoperazone, Cephtriaxone, 4th Generation Cephalosporins, Cefepime, Tetracyclines, Tetracycline, Minocycline, Doxycycline, Macrolides, Azithromycin, Erithromycin, Clarithromycin, Lincosamides/Lincosamines, Clindamycin (Cleocin), Sulfonamides/Sulfa Drugs, Sulfamethoxazole–Trimethoprim (generic), (Bactrim), (Cotrim), (Septra), Fluoroquinolones, Ciprofloxacin (Cipro), Norfloxacin, Ofloxacin, Levofloxacin, Aminoglycosides, Streptomycin, Tobramycin, Gentamycin, Amikacin.

In some embodiments of the invention, the antimicrobial agent is an antibacterial agent. While any antibacterial agent may be used in the preparation of the instant antimicrobial solutions, some non-limiting exemplary antibacterial agent (s) include those classified as aminoglycosides, beta lactams, quinolones or fluoroquinolones, macrolides, sulfonamides, sulfamethaxozoles, tetracyclines, streptogramins, oxazolidinones (such as linezolid), clindamycins, lincomycins, rifamycins, glycopeptides, polymxins, lipo-peptide antibiotics, as well as pharmacologically acceptable sodium salts, pharmacologically acceptable calcium salts, pharmacologically acceptable potassium salts, lipid formulations, derivatives and/or analogs of the above.

The solvent used in the present invention include, but are not limited to acetone, chloroform, dichloromethane, dimethylsulfoxide, dimethyl formamide, polyethylene glycol, or N-Methyl-2-Pyrrolidone (NMP).

The non-solvent used in the present invention include, but are not limited to ethanol, methanol, water, cyclohexane, hexane, pentane, hydrogen peroxide, diethyl ether, tert-butyl methyl ether (TBME), phosphate buffer saline solution (PBS), or a mixture thereof.

Suitable additives include, but are not limited to growth factors, vitamins, peptides, biologics, amino acids, antibiotics, and antiviral agents.

In another embodiment, additives include, but are not limited to Alendronate, Olpadronate, Etidronate, Colecalciferol (vitamin D), Tocopherol (vitamin E), Pyridoxin (vitamin B6), Cobalamine (vitamne B12) Platelet-derived growth factor (PDGF), Glycine, Lysine, penicillin, cephalosporin, tetracycline, lamivudine, and zidovudine.

In some embodiments of the invention, the additive is a curing agent. The curing agent include, but are not limited to, thiol, alcohol, and amine functional groups. Preferred curing agents are multifunctional molecules. A curing agent can assist in formation of a strong adhesive bond by facilitating crosslinking throughout the material. The curing agent can accelerate the curing process of the adhesive by reacting with the polymer functional groups. Preferably, the curing agent forms covalent bonds with the polymer functional groups. Curing agents generally do not react with the substrate.

The multifunctional molecules can, for example, include at least one of polyethylene glycol, a polyamino acid (typically, greater than 50 linked amino acids and including, for example, proteins and/or polypeptides), an aliphatic polyester (including, for example, polylactic acid, polyglycolic acid and/or polycaprolactone), a saccharide (including, for example, a sugar), a polysaccharide (for example, starch), an aliphatic polycarbonate, a poly amine (including, for example, Polyethylenimine), a polyanhydride, a steroid (for example, hydrocortisone), glycerol, ascorbic acid, an amino acid (for example, lysine, tyrosine, serine, and/or tryptophan), or a peptide (typically, 2 to 50 linked amino acids), an inorganic particle (for example bioglass, hydroxyapatite, ceramic particles).

In one embodiment, the curing agent present in the non-solvent include, but are not limited to, poly-ethyleneimine (PEI), poly-l-lysine (PLL), poly-d-lysine (PDL), poly-d,l-lysine (PDLL), poly-l-cysteine, poly-d-cysteine, poly-d,l-cysteine, short oligomers of l-lysine, d-lysine, l-cysteine, d-cysteine, amino functionalized PEG, amino functionalized inorganic particles (bioglass, hydroxyapatite, tetracalcium phosphate), and tin catalysts.

The molecular weight of polymers used as curing agents is between 1 to 500 kDa. Preferably, the molecular weight of polymers used as curing agents is between 150 and 300 kDa.

The number of residues present in the short oligomers used as curing agents is between 3 and 20. Preferably, residues present in the short oligomers used as additives is between 4 and 15.

The concentration of the curing agents is between 0.1 and 50 g/l. Preferably, the concentration of the curing agents is between 1 and 10 g/l.

In an embodiment, the linker is the combination of various covalent bonds including, but are not limited to, carboxylic ester, carbonate, carbamate (urethane), carbamide (urea), amide, sulfide, and disulfide. In other embodiments of the invention, the linker may contain mixed functional linkages for the conjugation of the functional group precursors.

Suitable linkers include, but are not limited to, dichloromethane (DCM), triethyl amine, and 1-Ethyl-3-(3-dimethylaminopropyl)carbodiimide (EDC).

The metal substrate used in the lap shear testing procedure include, but are not limited to, titanium, nitinol, magnesium, stainless steel, and cobalt/chromium alloys.

The medical implantable substrate used in the lap shear testing procedure include, but are not limited to, PEEK, PLA, hydroxyapatite, and calcium phosphate.

The typically degradation profiles of Formula A, Formula B, Formula C, Formula D, or a mixture thereof that is mixed with curing agent can be at least two weeks, at least one month, at least 3 months, at least 6 months, at least 9 months, at least 12 months, at least 18 months, or at least 24 months.

In an oral application, the polymer backbone, Formula A, Formula B, Formula C, Formula D, or a mixture thereof can be used for dental membrane applications. The membrane can be placed over the bone but under the gum tissue. In solution 1, polymer backbone, Formula A, Formula B, Formula C, Formula D, or a mixture thereof can be dissolved in a solvent. In solution 2, an additive can be dissolved in a non-solvent. In another embodiment, solution 2 contains a non-solvent only. In one embodiment, solution 1 and solution 2 can be applied to the site simultaneously by using separate syringes. In another embodiment, solution 1 and solution 2 can be applied to the site using two syringes that are connected to an applicator tip dual cannula. Once solution 1 and solution 2 are in physcial contact, the dissolved bioresorbable polymer precipitates out from the solution to form a gel. The rest of the solvent can be cleaned and the gel like polymer will be present on the site between bone and the gum. In one embodiment, the ratio of solution 1 to solution 2 is 1:1. In another embodiment, the raito of solution 1 to solution 2 is 2:1 to 1:10.

In a 3D printing application, the method of producing a 3D printed part with the polymer backbone, Formula A, Formula B, Formula C, Formula D, or a mixture thereof includes making a polymer solution with the said polymers to be printed. The polymer solution is prepared and stored in a cartridge compatible with the 3D printer. The additive solution is prepared and stored in appropriate conditions. A solid model is developed with the desired print geometry. The solid model is prepared for printing by performing a 'slicing' operation. The slicing operation separates the solid part geometry into the multiple layers that the printer is going to print. The layer height of the slices is determined by the operator and tip opening diameter. A petri dish mount is secured to the platform. The petri dish used as a printing surface is placed within the mount. The prepared print geometry file is imported into the 3D printer software. The print is prepared by assigning a material to be used for the print and assigning a pattern to be used for the print infill. Additional factors are altered in this stage for the printing operation, but the two most basic changes are assigning a material to print with and a pattern for the print infill. A tip of desired diameter is added to the polymer solution cartridge and the cartridge is placed into the print head of the 3D printer. The printing surface of the petri dish is prepared by spraying a uniform layer of the additive. The print head containing the polymer solution is calibrated, and initial printing parameters are estimated and placed into the material profile in the 3D printer software. The printing operation is started by the operator. The printing head of the 3D printer moves in the x and y direction to print the part geometry. In-between layers, the polymer is allowed to cure for a minimum of 30 seconds. The print head then raises (z) and prints the next layer of the geometry. This process is repeated until the entire part has been printed.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Compounds of Formula A, B, C, and D may be prepared according to the following reaction schemes. In general the compounds of this invention can be made by processes which include processes analogous to those known in the chemical arts, particularly in light of the description contained therein. Certain processes for the manufacture of the compounds of this invention are provided as further features of the invention and are illustrated by the following reaction schemes.

Preparation of Example 1

Synthesis of the PEG-PLGA-PEG Backbone (Polymer Backbone)

Scheme 1 depicted in FIG. 1 refers to the preparation of the PEG-PLGA-PEG backbone. To a molten mixture of D,L lactide (601.3 g, 4.17 mol) and glycolide (149.0 g, 1.28 mol), glycolic acid (18.9 g, 0.25 mol) was added by means of a glass funnel. The mixture was stirred for 10 minutes and then a solution of Tin(II) 2-ethylhexanoate (0.2309 g, 0.57 mmol) in toluene (5 ml) was added by means of a syringe. Immediately after the addition, the reactor temperature was set at 170° C. After 3 hours and 30 minutes, succinic anhydride (124.3 g, 1.24 mol) was added and the melted mixture was stirred at 170° C. for 2 hours. The reactor was then evacuated slowly until full vacuum was reached and kept under vacuum for an additional 2 hours. The reactor was purged with nitrogen. The polymer was poured into a pan and cooled with liquid nitrogen. The obtained crude material (736 g) was then dried under vacuum at room temperature. (vacuum is −28 inch/Hg) and purified by precipitation (Water/Acetone ratio. 20:1) to yield a clean product. Overall yield was 70%.

In a 500 ml reactor equipped with a mechanical stirrer PEG (9.76 g, 24.4 mmol) and 1,3-dicyclohexyl carbodiimide (DCC, 3.79 g, 18.3 mmol) were added to a solution of carboxylic acid-terminated PLGA (II, 20 g, 6.68 mmol) in dichloromethane (DCM, 200 ml). After stirring the solution for 10 minutes, 4-dimethyl amino pyridine (DMAP, 2.24 g, 18.3 mmol) was added and the reaction mixture was stirred for 12 hours at room temperature. The precipitated dicyclohexyl urea was filtered off, the solution was poured into cold diethyl ether, and the precipitate were filtered and washed with diethyl ether. The sticky viscous solid was then dried under vacuum at room temperature for 2 days. A sticky white-off solid (product III) was then obtained with an overall yield of 80%.

In a 500 mL reactor, substrate III (10 g, 2.5 mmol) and succinic anhydride (15 g, 15 mmol) were dissolved in dichloromethane (100 mL) and stirred for 18 hours at 60° C. The polymer was then precipitated in cold diethyl ether (400 mL) and washed with ethanol and diethyl ether. The greasy solid was then dried under vacuum to yield off-white solid (product IV) with overall yield of 80%.

Preparation of Example 2

Synthesis of Formula I, wherein R is

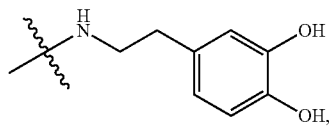

also known as Formula A

Figure 2:
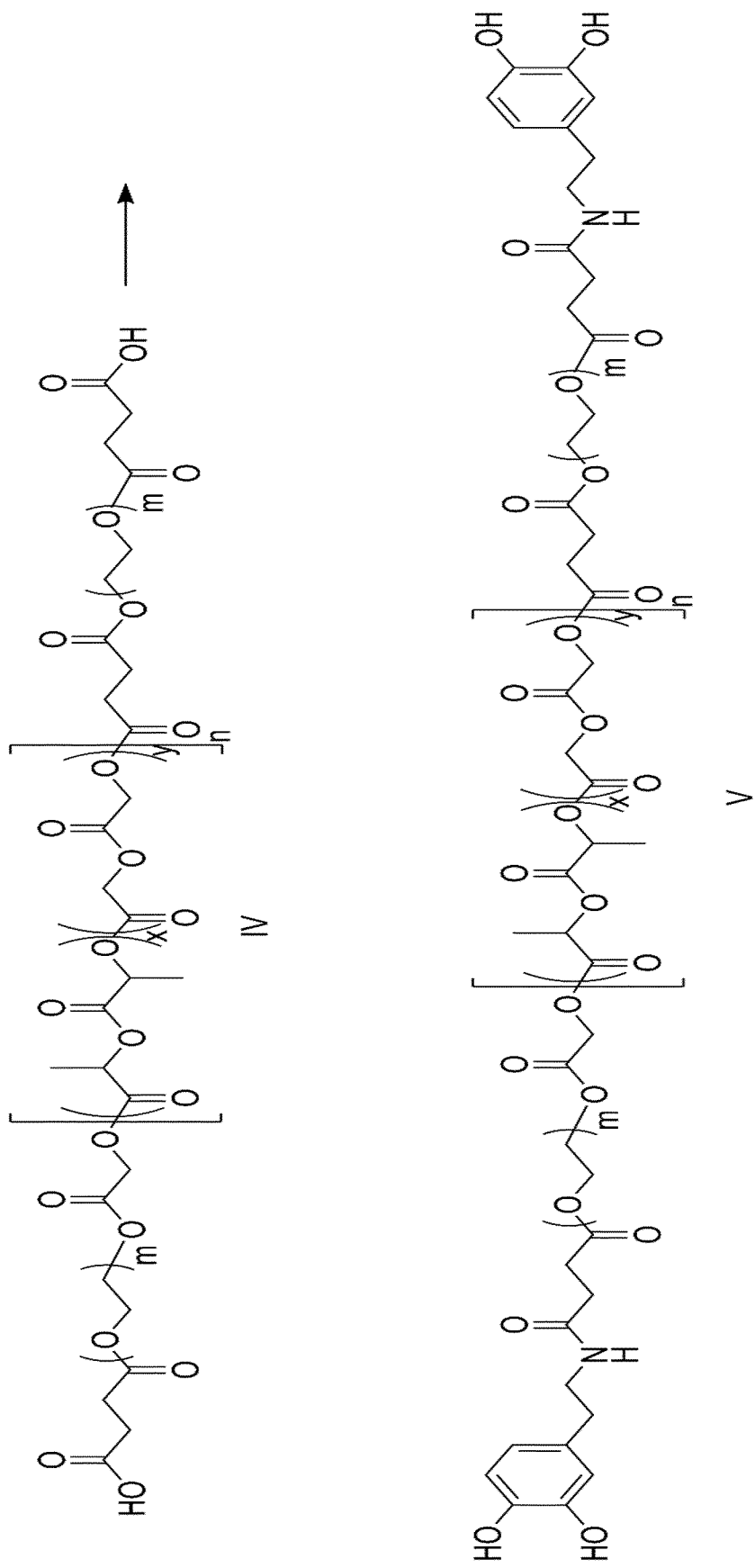
FIG. 2 is a reaction scheme showing the synthesis of Formula A.

Scheme 2 depicted in FIG. 2 refers to the preparation of Formula A. In a 50 ml round bottom flask, dopamine hydrochloride (0.356 g, 1.88 mmol) was dissolved in dichloromethane in presence of triethyl amine (TEA, 0.26 ml, 1.88 mmol) and stirred for 10 minutes at room temperature. In a separate flask, carboxylic acid-terminated PEG-PLGA-PEG (IV) (3 g, 0.75 mmol) and 1,3-dicyclohexyl carbodiimide (DCC, 0.387 g, 1.88 mmol) were dissolved in dichloromethane (DCM, 10 ml). The two solutions were then combined and 4-dimethyl amino pyridine (DMAP, 0.23 g, 1.88 mmol) was added. This solution was then stirred for 12 hours in reflux conditions. The formed precipitate dicyclohexyl urea was filtered off and the reaction mixture was poured into cold diethyl ether. The precipitate was filtered, washed with ethanol and dried under vacuum at room temperature for 2 days to yield product V.

Preparation of Example 3

Synthesis of Formula I, wherein R is

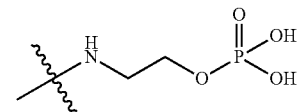 [SMILES: *NCCOP(=O)(O)O]

or

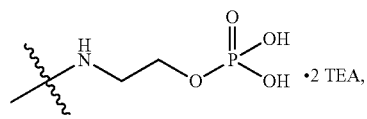 [SMILES: *NCCOP(=O)(O)O]

2 TEA, also known as Formula B

Figure 3:
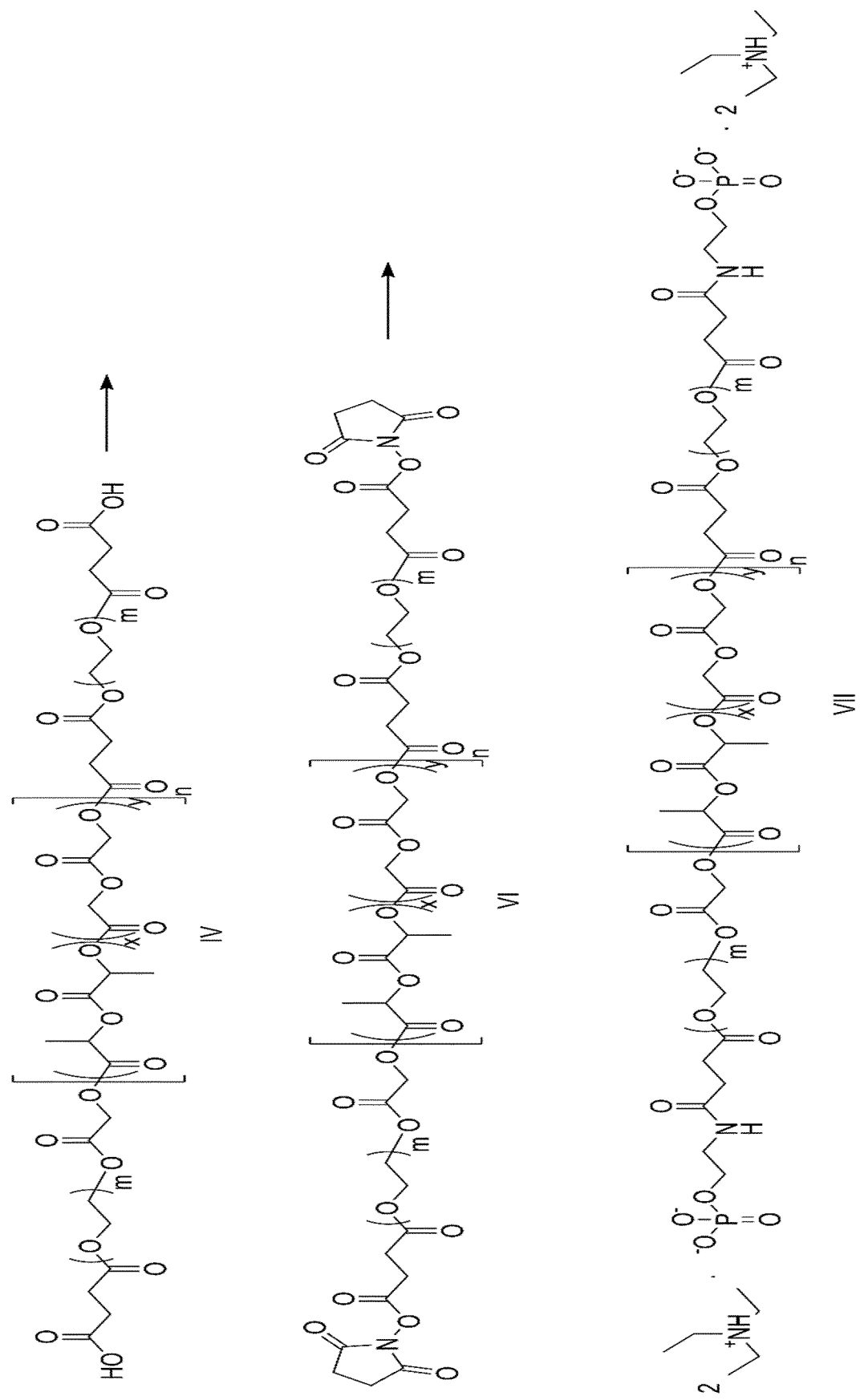
FIG. 3 is a reaction scheme showing the synthesis of Formula B.

Scheme 3 depicted in FIG. 3 refers to the preparation of Formula B. In a 500 ml reactor equipped with a mechanical stirrer, carboxylic acid-terminated PEG-PLGA-PEG (IV) (10 g, 2.5 mmol) and 1,3-dicyclohexyl carbodiimide (DCC, 1.9 g, 9.15 mmol) was dissolved in dichloromethane (DCM, 100 ml). To this solution, NHS (1.05 gram, 9.15 mmol) was added. This solution was stirred for 12 hours in reflux conditions. The formed precipitate dicyclohexyl urea was filtered off and the reaction mixture was poured into cold diethyl ether. The precipitate was filtered, washed with ethanol and dried under vacuum at room temperature for 2 days to yield product VI.

In a round bottom flask O-Phosphoriylethanolamine (0.082 g, 0.58 mmol) and triethyl amine (0.118 g, 1.17 mmol) were dissolved in 1.5 ml of water. In a separate round bottom flask, Product VI (1 g, 0.26 mmol) was dissolved in 10 ml of tetrahydrofuran. Both solutions resulted in a clear color. After 10 minutes, the O-Phosphoriylethanolamine solution was added to the Product VI solution. A light precipitate was formed. To the final suspension, 4 ml of acetonitrile was added. A biphasic suspension formed. The suspension was stirred for 18 hours at room temperature. The two phases were separated. The solvent of the upper phase was removed under reduced pressure to give a white solid. The obtained material was then dried by dissolving and drying the powder with acetone, diethyl ether and DCM. The final DCM solution was then poured in 35 ml of diethyl ether. The formed suspension was centrifuged and the solid material dried under vacuum to give 0.7 gram of Product VII.

Preparation of Example 4

Synthesis of Formula I, wherein R is

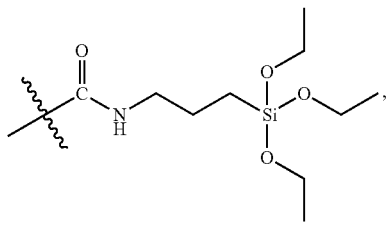 [SMILES: *C(=O)NCCC[Si](OCC)(OCC)OCC]

also known as Formula C

Figure 4:
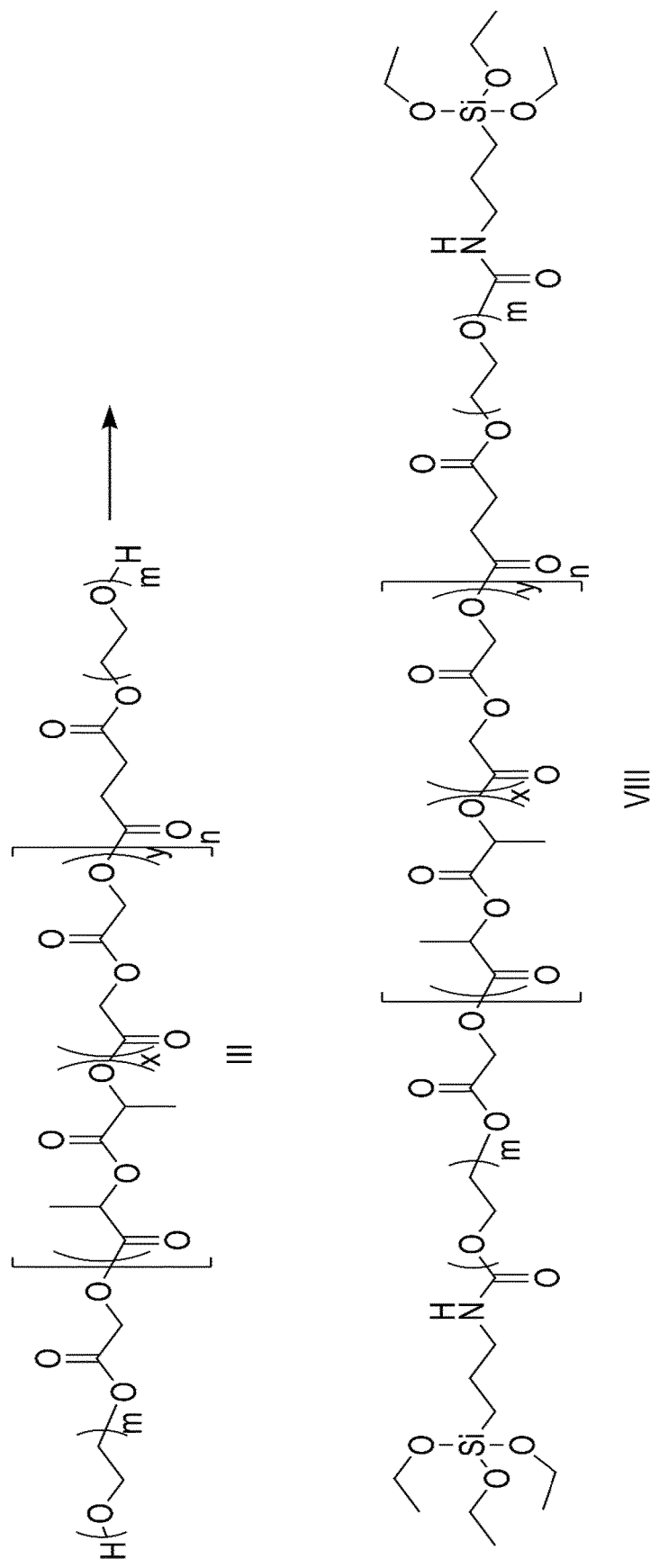
FIG. 4 is a reaction scheme showing the synthesis of Formula C.

Scheme 4 depicted in FIG. 4 refers to the preparation of Formula C. In a PTFE round-bottom flask, substrate III (2 g, 0.53 mmol) and triethylamine (0.3 ml, 2.1 mmol), were dissolved in 20 mL of tetrahydrofuran. To the clear solution, triethoxysilylpropylisocyanate (0.26 mL, 1.05 mmol) was added dropwise and the reaction mixture was stirred at reflux temperature for 12 hours. The reaction was then allowed to equilibrate to room temperature. 6 ml of ethanol was added and the solution was stirred at room temperature for 16 hours. Afterwards the solvent was evaporated under reduced pressure. The residual oil was dissolved in 6 ml of DCM and the solution was poured into diethyl ether. The precipitate was isolated and dried under vacuum for 8 hours to yield 1.8 gram of white solid (Product VIII).

Preparation of Example 5

Synthesis of Formula I, wherein R is

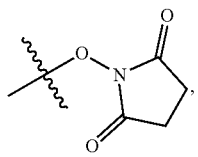 [SMILES: *ON1C(=O)CCC1=O]

also known as Formula D

Figure 5:
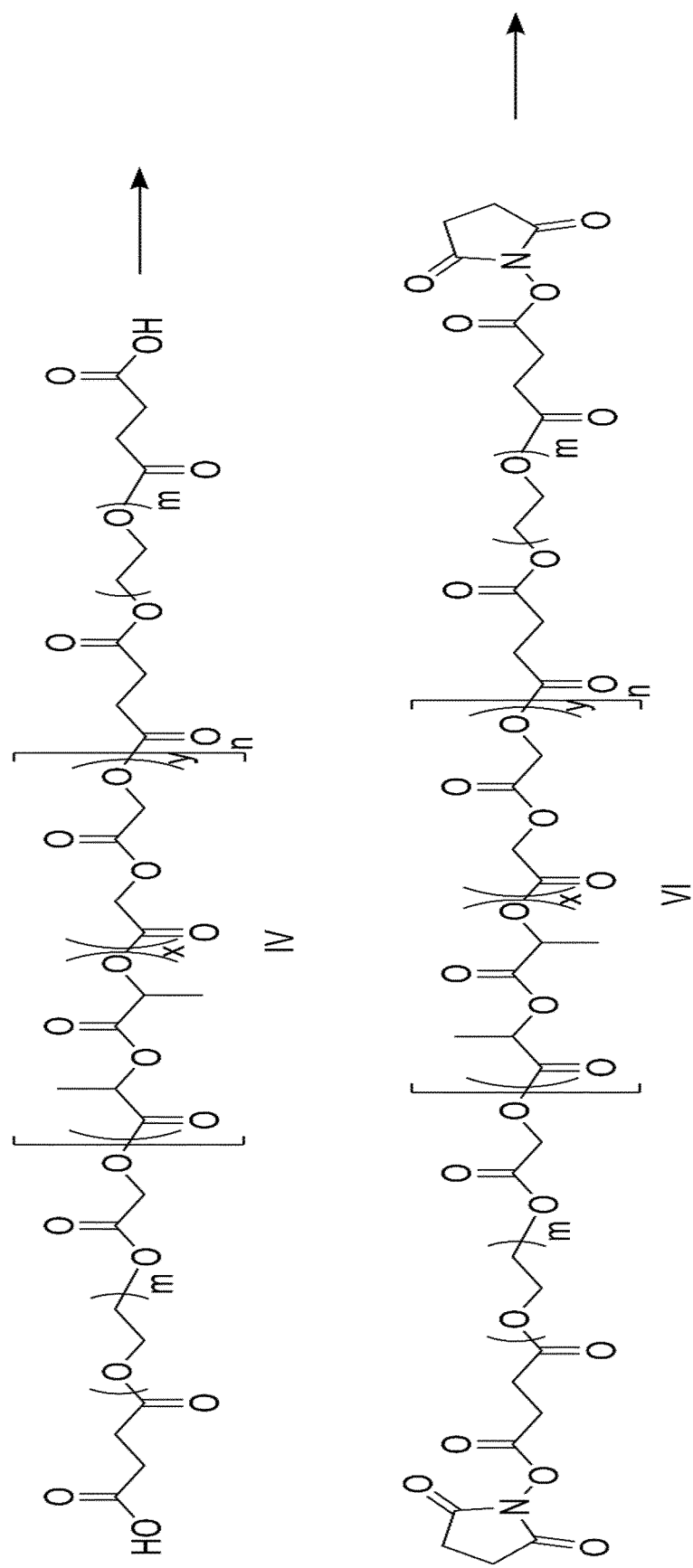
FIG. 5 is a reaction scheme showing the synthesis of Formula D.

Scheme 5 depicted in FIG. 5 refers to the preparation of Formula D. In a 500 ml reactor equipped with a mechanical stirrer, carboxylic acid-terminated PEG-PLGA-PEG (IV) (10 g, 2.5 mmol) and 1,3-dicyclohexyl carbodiimide (DCC, 1.9 g, 9.15 mmol) was dissolved in dichloromethane (DCM, 100 ml). To this solution NHS (1.05 gram, 9.15 mmol) was added. This solution was stirred for 12 hours in reflux conditions. The formed precipitate dicyclohexyl urea was filtered off and the reaction mixture was poured into cold diethyl ether. The precipitate was filtered, washed with ethanol and dried under vacuum at room temperature for 2 days to yield product VI.

NMR Data for the Bioresorbable Polymers and Testing Results

Table 1 refers to the NMR data for the bioresorbable polymers.

TABLE 1

| Structure | 1H-NMR (CDCl$_3$, 400 MHz) |
| --- | --- |
| PEG-PLGA-PEG backbone | 1.5-1.65 (br, 3H), 2.65-2.8 (br, 12H), 3.6-3.8 (br, 8H), 4.2-4.4 (br, 8H), 4.6- |

TABLE 1-continued

| Structure | 1H-NMR (CDCl$_3$, 400 MHz) |
| --- | --- |
| (polymer backbone) | 4.9 (br, 2H), 5.1-5.3 (br, 1H) |
| Formula A | 1.5-1.65 (br, 3H), 2.65-2.8 (br, 12H), 3.6-3.8 (br, 8H), 4.2-4.4 (br, 8H), 4.6-4.9 (br, 2H), 5.1-5.3 (br, 1H), 6.5-7.2 (br, 6H), 7.6-7.8 (br, 2H) |
| Formula B | 1.30 (t, 18H, J = 7.35 Hz), 1.5-1.65 (br, 3H), 2.5-2.6 (br, 2H), 2.6-2.8 (br, 12H), 3.09 (q, 12H, J = 7.46 Hz), 3.45-3.5 (br, 4H), 3.6-3.8 (br, 8H), 3.9-4.0 (br, 4H), 4.2-4.4 (br, 8H), 4.6-4.9 (br, 2H), 5.1-5.3 (br, 1H), 7.2-7.3 (br, 2H) 31P-NMR (CDCl$_3$, 161 MHz): 2.165 ppm |
| Formula C | 0.6-0.7 (br, 4H), 1.2-1.25 (br, 18H), 1.5-1.65 (br, 3H), 2.6-2.8 (br, 4H), 3.1-3.2 (br, 4H), 3.6-3.8 (br, 4H), 3.83 (q, 12H), 4.2-4.3 (br, 4H), 4.6-4.9 (br, 2H), 5.1-5.3 (br, 1H) |
| Formula D | 1.4-1.6 (br, 3H), 2.5-3.0 (br, 12H), 2.8 (br, 8H), 3.5-37 (br, 8H), 4.1-4.3 (br, 8H), 4.6-4.9 (br, 2H), 5.1-5.3 (br, 1H) |

The biodegradable polymers were tested for the shear strength of its adhesive properties under both dry and wet conditions on bone analogue substrates, or on bone analogue substrate and metal substrate.

Testing in Dry Conditions

The bone analogue substrates were obtained from Bone-Sim Laboratories, from the Cancellous Bovine Bones 1200 series (Density: 1.2 g/cc, Dimension 10×10×40 mm, cyanoacrylate binder 5-7%). 100 to 200 mg of the biodegradable polymer were dissolved in 0.1 to 1 mL of dichloromethane to give a clear solution. The formed solution was then loaded into a 1 ml syringe (Henke Sass Wolf 1 ml NORM-JECT®—Tuberkulin). A second 5 ml syringe (Henke Sass Wolf 5 ml (6 ml) NORM-JECT®) was loaded with diethyl ether. The two liquids were pushed out of the syringes onto the surface of a first bone analogue substrate and allowed to passively mix to form a viscous gel. The gel was spread out on a surface of 15×10 mm on the first bone analogue substrate, and was dried for a period of 16 hours under reduced pressure (5 Torr ca.). Afterwards, a second bone analogue substrate (with the same dimensions as the first one) was put on top of the first bone analogue substrate on the 15×10 mm surface where the gel was spread. A 1.2 kg weight was laid on top of the two glued together bone analogue substrates for at least 16 hours. The prepared specimen was then tested using the lap shear procedure.

Shear strength of the adhesive materials were determined by a single-lap-joint specimen. The contact area of the glued bone analogous substrates (15×10 mm ca.) was measured and kept as a reference for the calculation of the final shear strength values. The specimens were then mounted on the tensile tester (Instron 3366 from Instron Corporation) equipped with a 10 kN load cell and pneumatic grips (air pressure is 10 PSI). The specimen was then pulled apart with speed of 5 mm/min to generate a shear force on the adhesive with no peeling force. The applied force needed to maintain the set pulling speed was then recorded. This protocol is similar to the protocol used in the "Standard Test Method for Strength Properties of Tissue Adhesives in Lap-Shear by Tension Loading" ASTM F2255 except modified for application in bone and metal substrates.

Testing in Wet Conditions on Bone Analogue Substrates

The same procedure was used as in the dry conditions, except that the bone substrates were previously immersed in distilled water for about 10 seconds prior to the start of the procedure.

Testing in Surgi-Heal Conditions on Bone Analogue Substrates

The same procedure was used as in the wet conditions, except that the 1 ml syringe was loaded with the biodegradable polymer solution in PEG 400, and the 5 ml syringe was loaded with 15% (w/w) of hydrogen peroxide in water.

Testing Following the Two Syringe Applicator with a Dual Cannula Tip Concept of the Surgi-Heal Glues In a 50 ml PE test tube, 0.3 g of bioresorbable polymer of Formula A, B, C, or D were dissolved in 0.6 ml of dry DMSO. After 2 h agitation by means of an agitation plate the solution became clear (solution 1:0.7 ml). The resulting solution was loaded into a 1 ml syringe. Meanwhile, 10 ml of D.I. Water and any eventual additive (e.g. Triethylamine, Poly-l-lysine, cross-linkers etc.) were loaded in a 12 ml syringe.

The two syringes were then connected to an applicator tip dual cannula (20 ga×2") and the two solutions were pushed by hand throughout the cannulas. The formed gel was then deposited on a surface of 20×25 mm of engineered bone analogues substrates (BoneSim, Cancellous bovine Bones with density 1.3 g/cc, dimensions following modified ASTM standard F2258, adhesion area 20×25 mm, cyanoacrylate binder<5%). Afterwards, a second bone substrate with the same characteristics of the previous one was approximated to the prepared substrate. Both bone specimens were previously soaked with D.I. water (immerged into D.I. water for about 10 Seconds). A weight of 1 Kg was then laid on such specimen and the system was let rest for 16 h. The so prepared specimen was then tested following tensile procedures.

Testing on Bone Analogue Substrate to Metal Substrate

The same procedure was used as in the dry conditions, except that the second bone analogue substrate was replaced with a metal substrate, which is stainless steel.

Table 2 refers to the values of the shear strength of the biodegradable polymers as measured using the lap shear procedure.

TABLE 2

| Condition | Biodegradable Polymer(s) | Shear Strength (MPa) | Substrate |
| --- | --- | --- | --- |
| Dry | Formula B | 0.28 | bone to bone |
| Dry | Formula B | 0.37 | bone to metal |
| Wet | Formula A/Formula B (1:1) | 0.24 | bone to bone |
| Wet | Formula C | 0.24 | bone to bone |
| Wet | Formula A/Formula B (1:1) in Surgi-Heal Conditions | 0.12 | bone to bone |

Table 3 refers to the values of the tensile strength of the biodegradable polymers prepared using the two syringe applicator with a dual cannula tip for the Surgi-Heal Glues and measured using tensile procedure.

TABLE 3

| Biodegradable Polymer(s) | Additive | Tensile Strength (MPa) |
| --- | --- | --- |
| Compound II (precursor) | N/A | 0.007 |
| Compound III (precursor) | N/A | 0.086 |
| FORMULA A | N/A | 0.183 |
| FORMULA B | N/A | 0.105 |
| FORMULA B/FORMULA A (1:1) | N/A | 0.024 |
| FORMULA C | N/A | 0.07 |
| FORMULA D | N/A | 0.178 |
| Compound III (precursor) | 0.1% Poly-L-lysine •HBr | 0.153 |
| Compound IV (precursor) | 0.1% Poly-L-lysine •HBr | 0.089 |
| FORMULA A | 0.1% Poly-L-lysine •HBr | 0.114 |
| FORMULA B | 0.1% Poly-L-lysine •HBr | 0.073 |
| FORMULA D | 0.1% Poly-L-lysine •HBr | 0.28 |
| FORMULA D/FORMULA D with different Mn (5:1) | 0.1% Poly-L-lysine •HBr | 0.18 |
| FORMULA D | 0.1% Poly-L-lysine •HBr at 37° C. | 0.113 |
| FORMULA D | 0.1% Poly-L-lysine •HBr at 37° C. physiological solution | 0.24 |
| FORMULA D | 0.1% Poly-L-lysine •HBr at 8° C. | 0.367 |
| FORMULA D | 0.1% Poly-L-lysine •HBr after 1 week | 0.72 |
| Compound III (precursor) | 1% Poly-L-lysine •HBr | 0.12 |
| Compound IV (precursor) | 1% Poly-L-lysine •HBr | 0.33 |
| FORMULA D | 1% Poly-L-lysine •HBr | 0.82 |
| FORMULA C | Tin (oct) 2 | 0.08 |
| FORMULA A | PEI | 0.07 |
| FORMULA D | Bioglass-NH$_2$ | 0.1 |
| FORMULA D | star PEG-NH$_2$ | 0.31 |
| FORMULA D | PEI | 0.075 |
| FORMULA D | LysLysLys | 0.2 |
| FORMULA D | hydroxyapatite | 0.02 |

Unless otherwise specified, adhesion tests were performed at room temperature and 16 hours after the preparation of the specimen.

Figure 6:
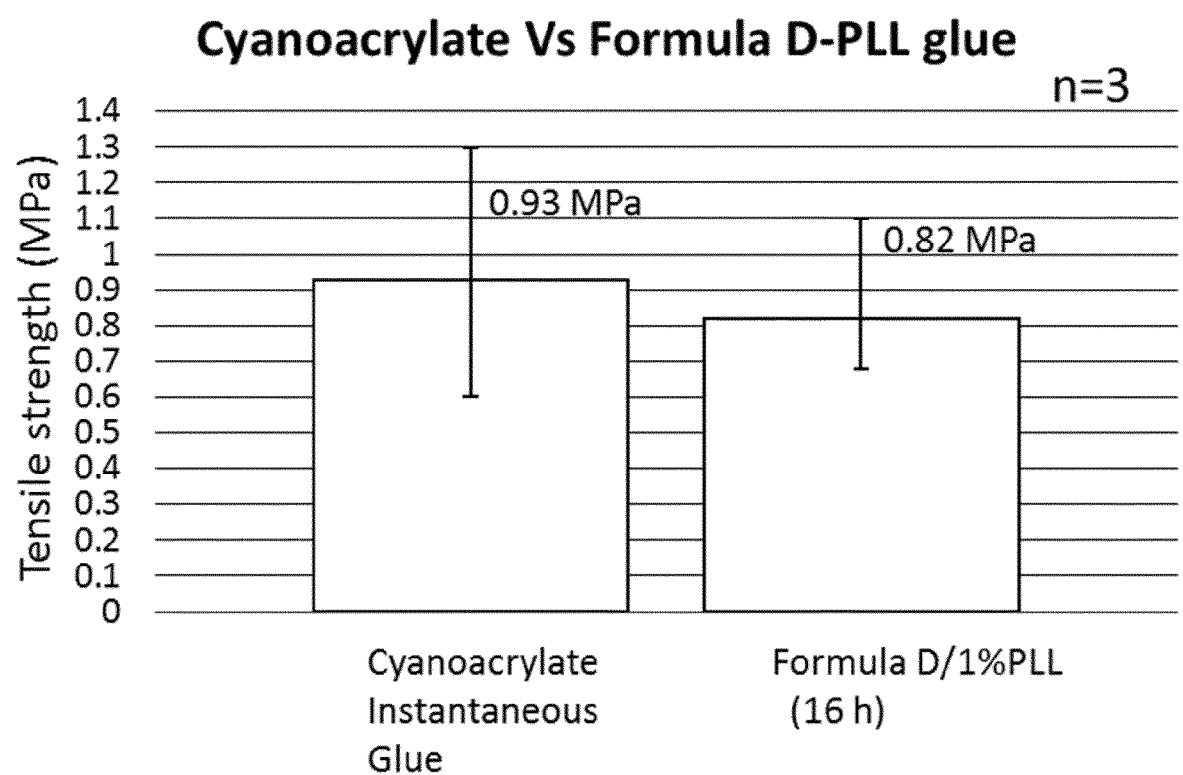
FIG. 6 shows the tensile strength of the composition of Formula D (Formula D/1% PLL) comparable to cyanoacrylate glue.
Figure 7:
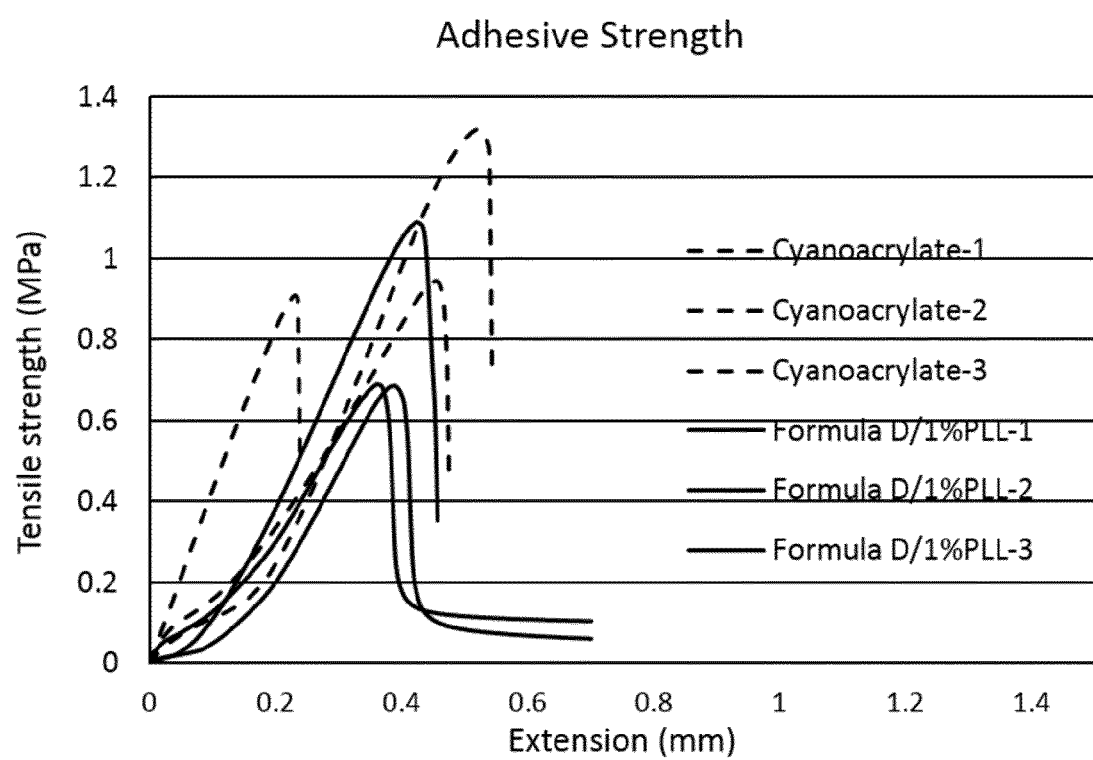
FIG. 7 shows the stress vs. strain plots of the composition of Formula D (Formula D/1% PLL) and cyanoacrylate glue.

Best formulation showed an average tensile strength of 0.82 MPa when the compound of Formula D was dissolved in DMSO with the concentration of 0.3 g of polymer in 0.6 ml of DMSO and 100 mg of poly-l-lysine hydrobromide (Mn=150-300 kDa) were dissolved in 10 ml of D.I. water. The clear solution of compound of Formula D in DMSO was loaded in the 1 ml syringe. The clear solution of poly-l-lysine in D.I. water was loaded in the 10 ml syringe. The two syringes were then connected to an applicator tip dual cannula (20 ga×2") and the two solutions were pushed by hand throughout the cannulas. The formed gel was then deposited on a surface of 20×25 mm of engineered bone analogues substrates (BoneSim, Cancellous bovine Bones with density 1.3 g/cc, dimensions following modified ASTM standard F2258, adhesion area 20×25 mm, cyanoacrylate binder<5%). Afterwards, a second bone substrate with the same characteristics of the previous one was approximated to the prepared substrate. Both bone specimens were previously soaked with D.I. water (immerged into D.I. water for about 10 Seconds). A weight of 1 Kg was then laid on such specimen and the system was left to rest for 16 h. Then the prepared specimen was tested following tensile procedures. Tests show a tensile strength comparable to cyanoacrylate glue tested following the same procedure as shown in the bar plot in FIG. 6 and Stress vs. Strain plots in FIG. 7.

Degradation Results of Bioresorbable Polymer 6 samples of polymer solutions (each containing 0.6 g Formula D and 20 ml of 0.1 w/v % poly-L-Lysine) was shaked at 140 rpm overnight. The samples were washed with water and dried thoroughly before the experiments. The samples each weighted around 0.5 g. Each sample was then placed into a falcon centrifuge tube filled with 30 mL of phosphate-buffered saline solution (1×PBS), pH 7.4. Sample charged tubes were then placed into an incubator at 37° C. for the time of the experiment. The pH of each solution was monitored every other day and the buffer solution was refreshed once the pH was lower than 7.2. At various time intervals, specifically at week 1, 2, 3, 4, 6 and 8, one of the tubes was analyzed to evaluate the occurred degradation. The material was removed from the incubator and equilibrated at room temperature for 1 hour. The sample was then centrifuged at 3000 rpm for 10 minutes to separate supernatant from polymers. The supernatant containing the soluble degradation products was collected and stored at −20° C. freezer for future studies, such as GPC, HPLC etc. In order to remove the salt residue from PBS buffer, the remaining material was washed with deionized water and centrifuged at 3000 rpm for 10 minutes for two times. The material was then collected and dried under vacuum until a constant weight was achieved (usually 48 hours). The weight loss was measured for each time point and sample was stored at −20° C. (freezer) before being submitted for GPC and NMR study.

Figure 8:
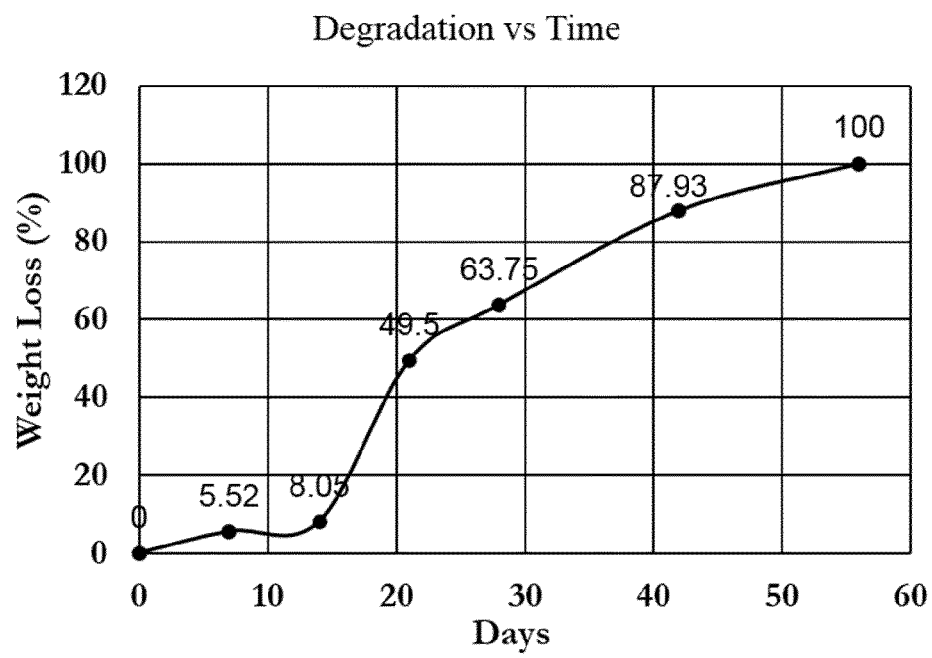
FIG. 8 shows the weight loss of the degradation of the composition of Formula D (Formula D/0.1% PLL) samples at various time intervals.

Table 4 refers to the weight loss of the polymer over the period of 0 to 56 days. Weight loss increased from 5.52% at day 7 to 100% degradation at week 8 (day 56). The burst degradation started on day 14 at 8.05% to 49.5% at day 21. The continuous degradation trend was observed at 63.75% on day 28 and 87.93% on day 42. The weight loss of the degradation samples at various time intervals are plotted in FIG. 8.

Figure 9:
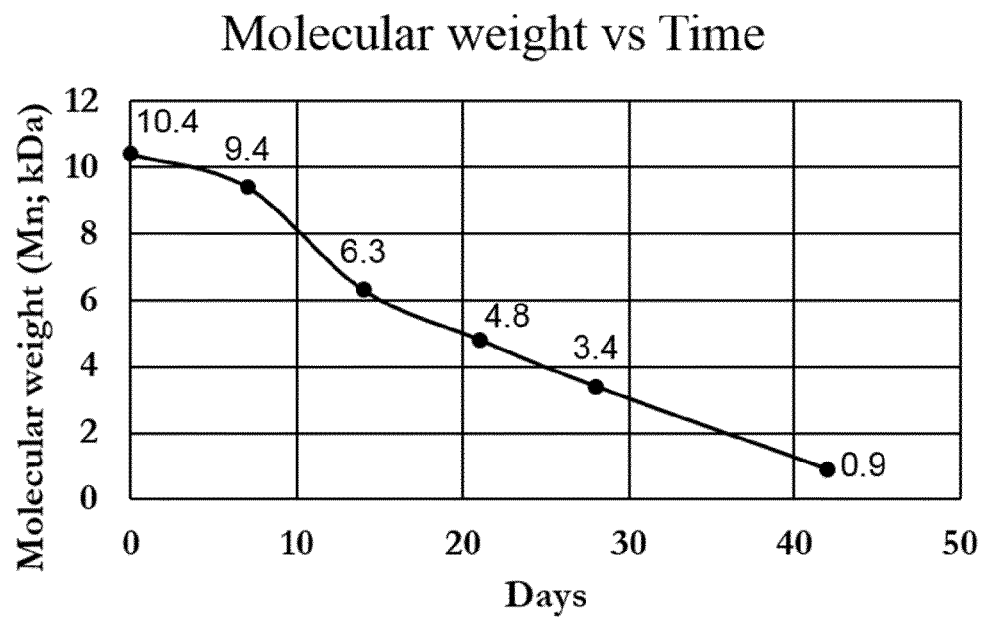
FIG. 9 shows the number-averaged molecular weight (Mn) of the degradation of the composition of Formula D (Formula D/0.1% PLL) samples at various time intervals.

Compared to the weight loss, the molecular weight decreased following the similar trend. The number-averaged molecular weight (Mn) of the degradation samples at various time intervals are plotted in FIG. 9.

TABLE 4

| Days | Weight loss (%) | GPC (Mn; kDa) | GPC (Mw; kDa) |
|---|---|---|---|
| 0 | 0 | 10.4 | N/A |
| 7 | 5.52 | 9.4 | 14 |
| 14 | 8.05 | 6.3 | 10 |
| 21 | 49.5 | 4.8 | 7.7 |
| 28 | 63.75 | 3.4 | 5.3 |
| 42 | 87.93 | 0.9 | 1.4 |
| 56 | 100 | 0 | 0 |

The molecular weight (Mn) decreased from the initial molecular weight of 10.4 kDa to 0.9 kDa after degrading for 6 weeks. After slightly slow degradation in the first 14 days, the molecular weight decreased to 6.3 kDa on day 14 and exhibit linear degradation trend until day 42. Very little material was left in the last sample on Day 56, and therefore; it was not possible to collect GPC data for this time point.

Example 6

3D Printing of Bioresorbable Polymer

The polymer solution (0.3 g of Formula D in 0.6 ml of DMSO) was prepared and stored in a cartridge compatible with the 3D printer (3D Bioplotter Manufacturing Series, manufactured by Envision Tec). 0.1% poly-l-lysine Hydrobromide solution in water (purchased from Sigma-Aldrich) was prepared and stored at 4° C. A solid model was developed of a tissue of area of 1 cm² with a height of a few layers. Then the solid model is prepared for printing by performing a 'slicing' operation. The slicing operation separated the solid part geometry into multiple layers for the printer to print. A petri dish mount was secured to the platform. The petri dish that was used as a printing surface was placed within the mount. The prepared print geometry file was imported into the 3D printer software. The print was prepared by assigning the polymer solution to be used for the print and assigned a pattern to be used for the print infill. A tip with the diameter of 0.4 mm was added to the polymer solution cartridge and the cartridge was placed into the print head of the 3D printer. The printing surface of the petri dish was prepared by spraying a uniform layer of the 0.1% poly-l-lysine Hydrobromide solution. The print head containing the polymer solution was calibrated, and initial printing parameters was estimated and placed into the material profile in the 3D printer software. The printing operation was started by the operator. The printing head of the 3D printer moved in the x and y direction to print the part geometry. In-between layers, the polymer was allowed to cure for a minimum of 30 seconds. The print head then raised (z) and printed the next layer of the geometry. This process was repeated until the entire part has been printed. The part was then dried.

Example 7A

Oral Application of Bioresorbable Polymer 0.3 g of polymer backbone was dissolved in 0.6 ml of DMSO to form Solution 1. Solution 2 contained 0.6 ml of water or 0.6 ml of phosphate-buffered saline (PBS) solution. Solution 1 and Solution 2 were applied to the site at the same time through two syringes that are connected to an applicator tip dual cannula. Solution 1 was contacted with Solution 2, which resulted in the dissolved polymer backbone to precipitate out from the solution to form a gel.

Example 7B

Oral Application of Bioresorbable Polymer 0.3 g of polymer of Formula D was dissolved in 0.6 ml of DMSO to form Solution 1. Poly-l-lysine (PLL) (0.1 w/v % poly-L-Lysine solution) was dissolved in 0.6 ml of water or 0.6 ml of phosphate-buffered saline solution to form Solution 2. Solution 1 and Solution 2 was applied to the site at the same time through two syringes that are connected to an applicator tip dual cannula. Solution 1 was contacted with Solution 2, which resulted in the dissolved polymer of Formula D to precipitate out from the solution to form a gel. Item 1 is a bioresorbable polymer of Formula I (Formula I)

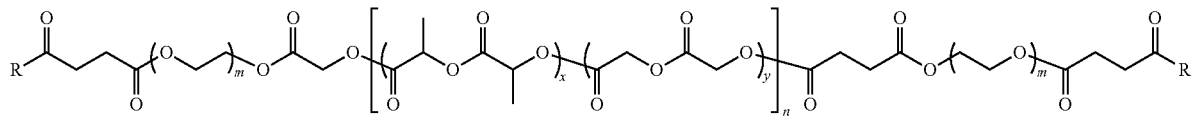

wherein:
R is:

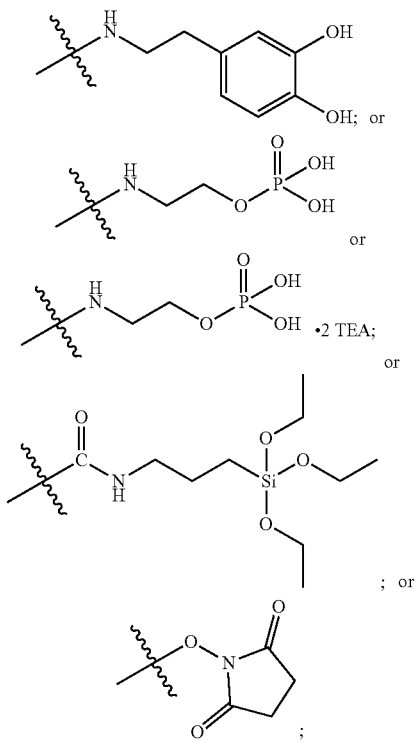

wherein:
m is between 4 and 90;
n is between 5 and 200;
x is between 1 and 200; and
y is between 0 and 200.

Item 2 is a composition comprising:
a bioresorbable polymer of Formula I of item 1, or a mixture thereof;
a solvent; and
a non-solvent.

Item 3 is the composition of item 2, wherein the composition further comprises an additive.

Item 4 is the composition of item 3, wherein the additive is dissolved in the non-solvent.

Item 5 is the composition of item 2 or 3, wherein the composition further comprises an antimicrobial agent, antibacterial agent, or a mixture thereof.

Item 6 is the composition of item 2 or 3, wherein the solvent is acetone, chloroform, dichloromethane, dimethylsulfoxide, dimethyl formamide, polyethylene glycol or N-Methyl-2-Pyrrolidone.

Item 7 is the composition of item 2 or 3, wherein the non-solvent is ethanol, methanol, water, cyclohexane, hexane, pentane, hydrogen peroxide, diethyl ether, tert-butyl methyl ether (TBME), phosphate buffer saline solution (PBS) or a mixture thereof.

Item 8 is the composition of item 3, wherein the additive is a growth factor, a vitamin, a biologic, an antibiotic, an antiviral agent, Alendronate, Olpadronate, Etidronate, Colecalciferol (vitamin D), Tocopherol (vitamin E), Pyridoxin (vitamin B6), Cobalamine (vitamne B12) Platelet-derived growth factor (PDGF), Glycine, Lysine, penicillin, cephalosporin, tetracycline, lamivudine, and zidovudine, polyethylene glycol, a polyamino acid (typically, greater than 50 linked amino acids and including, for example, proteins and/or polypeptides), an aliphatic polyester (including, for example, polylactic acid, polyglycolic acid and/or poly-caprolactone), a saccharide (including, for example, a sugar), a polysaccharide (for example, starch), an aliphatic polycarbonate, a poly amine (including, for example, Polyethylenimine), a polyanhydride, a steroid (for example, hydrocortisone), glycerol, ascorbic acid, an amino acid (for example, lysine, tyrosine, serine, and/or tryptophan), or a peptide (typically, 2 to 50 linked amino acids), an inorganic particle (for example bioglass, hydroxyapatite, ceramic particles), poly-ethyleneimine (PEI), poly-l-lysine (PLL), poly-d-lysine (PDL), poly-d,l-lysine (PDLL), poly-l-cysteine, poly-d-cysteine, poly-d,l-cysteine, short oligomers of l-lysine, d-lysine, l-cysteine, d-cysteine, an amino functionalized PEG, an amino functionalized inorganic particle (bioglass, hydroxyapatite, tetracalcium phosphate), and a tin catalyst.

Item 9 is a process for preparing a bioresorbable polymer of Formula I of item 1 comprising the steps of mixing a polymer backbone with a functional group precursor to form a mixture; and adding a linker to the mixture to form the bioresorbable polymer.

Item 10 is the use of composition according to one of items 1 to 8 as an adhesive for adhering material.

Item 11 is the use according to item 10, characterized in that the material is biological tissue.

Item 12 is the use according to item 10, characterized in that the material is biological tissue substrate and bone substrate.

Item 13 is the use according to item 10, characterized in that the material is metal substrate and bone substrate.

Item 14 is the use according to item 10, characterized in that the material is metal substrate and biological tissue.

Item 15 is the use according to item 10, characterized in that the material is metal substrate.

Item 16 is a method for filling void spaces within biological tissues comprising administering an amount of the composition according to item 2 or 3 to the void spaces within biological tissues.

Item 17 is a method for filling void spaces within biological tissues in oral cavities comprising administering an amount of a composition according to item 2 or 3 to the void spaces within biological tissues in oral cavities.

Item 18 is a method for administering an amount of a composition according to item 2 or 3 and a bioactive agent using a two syringe applicator with a dual cannula tip.

Item 19 is a dental membrane comprising a polymer backbone, a bioresorbable polymer of Formula I of item 1, or a mixture thereof; a solvent; and a non-solvent.

Item 20 is a 3D printed part comprising polymer a backbone, a bioresorbable polymer of Formula I of item 1, or a mixture thereof; a solvent; a non-solvent; and additive.

Item 21 is a process for producing a 3D printed part containing a polymer backbone, a bioresorbable polymer of Formula I of item 1, or a mixture thereof; the process comprising:
(a) providing polymer backbone bioresorbable polymer of Formula I of item 1, or a mixture thereof;
(b) adding polymer backbone, bioresorbable polymer of Formula I of item 1, or a mixture thereof to a solvent to form a polymer solution;
(c) adding or contacting an additive to the polymer solution;
(d) printing the polymer solution through a print head to form multiple layers of the 3D printed part; and
(e) setting the 3D printed part.

Item 22 is a bioprinted part comprising a polymer backbone, a bioresorbable polymer of Formula I of item 1, or a mixture thereof; a solvent; a non-solvent; an additive; and a bioactive agent.

Item 23 is a process for producing a bioprinted part containing a polymer backbone, a bioresorbable polymer of Formula I of item 1, or a mixture thereof; the process comprising:

(a) providing polymer backbone, bioresorbable polymer of Formula I of item 1, or a mixture thereof;

(b) adding polymer backbone, bioresorbable polymer of Formula I of item 1, or a mixture thereof to a solvent to form a polymer solution;

(c) adding or contacting an additive to the polymer solution;

(d) printing the polymer solution through a print head to form multiple layers of the bioprinted part;

(e) setting the bioprinted printed part;

and wherein either step (b) or (c) further comprises adding a bioactive agent.

What is claimed is:

1. A bioresorbable polymer of Formula I

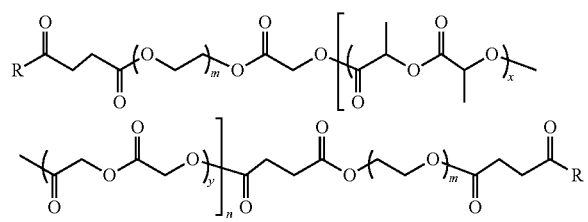

(Formula I)

wherein:
R is:

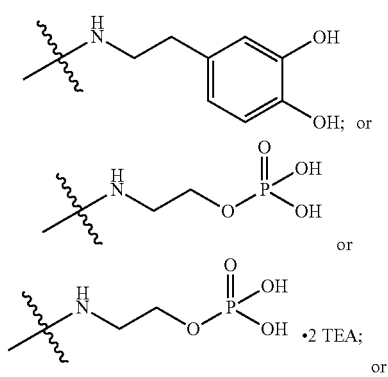

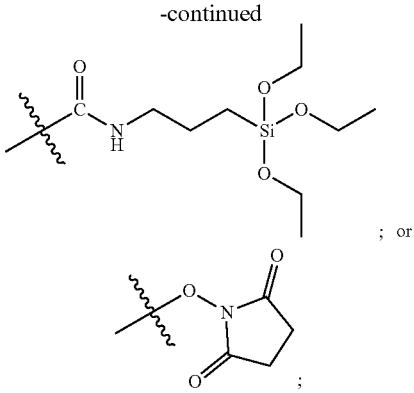

wherein:
m is between 4 and 90;
n is between 5 and 200;
x is between 1 and 200; and
y is between 0 and 200.

2. A composition comprising:
a bioresorbable polymer of Formula I of claim 1, or a mixture thereof;
a solvent; and
a non-solvent.

3. The composition of claim 2, wherein the composition further comprises an additive.

4. The composition of claim 3, wherein the additive is dissolved in the non-solvent.

5. The composition of claim 2, wherein the composition further comprises an antimicrobial agent, antibacterial agent, or a mixture thereof.

6. The composition of claim 2, wherein the solvent is acetone, chloroform, dichloromethane, dimethylsulfoxide, dimethyl formamide, polyethylene glycol or N-Methyl-2-Pyrrolidone.

7. The composition of claim 2, wherein the non-solvent is ethanol, methanol, water, cyclohexane, hexane, pentane, hydrogen peroxide, diethyl ether, tert-butyl methyl ether (TBME), phosphate buffer saline solution (PBS) or a mixture thereof.

8. The composition of claim 3, wherein the additive is a growth factor, a vitamin, a biologic, an antibiotic, an antiviral agent, Alendronate, Olpadronate, Etidronate, polyethylene glycol, a polyamino acid, an aliphatic polyester, a saccharide, an aliphatic polycarbonate, a poly amine, a polyanhydride, a steroid, glycerol, ascorbic acid, an amino acid, or a peptide, an inorganic particle, poly-ethyleneimine (PEI), poly-l-lysine (PLL), poly-d-lysine (PDL), poly-d,l-lysine (PDLL), poly-l-cysteine, poly-d-cysteine, poly-d,l-cysteine, short oligomers of l-lysine, d-lysine, I-cysteine, d-cysteine, an amino functionalized PEG, an amino functionalized inorganic particle, and a tin catalyst.

* * * * *